United States Patent
Zhang et al.

[19]

[11] Patent Number: 6,043,360
[45] Date of Patent: Mar. 28, 2000

[54] INTERMEDIATES AND A PROCESS FOR PREPARING BENZO[B]THIOPHENES

[75] Inventors: Tony Yantao Zhang; John Paul Gardner, both of Indianapolis, Ind.

[73] Assignee: Eli Lilly and Company, Indianapolis, Ind.

[21] Appl. No.: 09/069,433

[22] Filed: Apr. 29, 1998

Related U.S. Application Data

[60] Provisional application No. 60/045,171, Apr. 30, 1997.

[51] Int. Cl.[7] ............... C07D 333/52; C07D 405/00; C07C 319/00; C07C 69/76
[52] U.S. Cl. ............... 540/596; 546/202; 548/525; 549/49; 549/51; 560/20; 560/55; 560/64; 560/65; 560/67; 560/73; 568/20; 568/38; 568/74; 568/75; 568/77
[58] Field of Search ............... 549/51, 49; 540/596; 546/202; 548/525; 568/38, 74, 75, 77, 20; 560/20, 64, 65, 67, 73, 55

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326 |
| 4,143,052 | 3/1979 | Barrault et al. | 360/329 |
| 4,358,593 | 11/1982 | Jones et al. | 546/202 |
| 4,380,635 | 4/1983 | Peters | 546/202 |
| 4,418,068 | 11/1983 | Jones et al. | 424/267 |
| 4,876,361 | 10/1989 | Claus-D et al. | 549/41 |
| 5,223,510 | 6/1993 | Gubin et al. | 514/299 |
| 5,395,842 | 3/1995 | Labrie et al. | 514/320 |
| 5,420,349 | 5/1995 | Godfrey | 564/74 |
| 5,470,854 | 11/1995 | Angerer et al. | 514/233 |
| 5,472,962 | 12/1995 | Sagamihara et al. | 514/233.5 |
| 5,482,949 | 1/1996 | Black et al. | 514/324 |
| 5,512,701 | 4/1996 | Hoard et al. | 556/428 |
| 5,552,412 | 9/1996 | Cameron et al. | 514/317 |
| 5,629,425 | 5/1997 | Labell et al. | 546/202 |

FOREIGN PATENT DOCUMENTS

| | | |
|---|---|---|
| 0062503 | 10/1982 | European Pat. Off. |
| 0062504 | 10/1982 | European Pat. Off. |
| 0275524 | 7/1988 | European Pat. Off. |
| 605 193 | 7/1994 | European Pat. Off. |
| 2097392 | 4/1982 | United Kingdom |
| 2096608 | 10/1982 | United Kingdom |
| 2097788 | 11/1982 | United Kingdom |
| WO 95/10513 | 4/1989 | WIPO |
| WO93/10741 | 6/1993 | WIPO |
| WO 89/0289 | 4/1995 | WIPO |
| WO95/10513 | 4/1995 | WIPO |

OTHER PUBLICATIONS

Richard, et al., *J. Am. Chem. Soc.* 118:12603–12613, 1996.
Ablenas, et al., *Can. J. Chem.* 65:1800, 1987.
Ogura, et al., *Synthesis*, 736–739, 1980.
Carlson, et al., *Acta Chema Scan.*, B41:164–173, 1987.
Jones, C.D., et al, *J. Med. Chem.* 27(8) 1057–1066 (1971).
Romeo Wagner, *Synthetic Organic Chemistry*, (171–172).
Jones, C.D., et al *J. Med Chem.* 35(5) 931–938 1992.
Kym, R.P. et al, *J. Med. Chem.*, 36 (24), 3911–3921.
Jackson, T.G., et al *J. Chem. Soc.* 1728–1729 (1969).
Kametani, et al *J. Org. Chem.* 41 (15) 2545–2547 (1976).
Crenshaw, R.R., et al *J. Med. Chem.* 14(12) 1185–1190 (1971).
Backstrom, et al, *J. Am. Chem. Soc.* 117 2351–2352 (1995).
Campaign, et al, *Chemical Abstracts* 50 (18) column 12981 (Sep. 25, 1956).
Von Angerer, et al *J. Steroid Biochem Molec. Biol.* 41 (No. 3–8) 557–562 (1992).
Eberle, et al *Chemical Abstracts* 73 (23) column 2, abstract No. 120318p (Sep. 1970).
Hoffman, et al *Chemical Abstracts* 117 (7) 765 column 1, abstract No. 69525b (Aug. 17, 1992).
Hoffman, et al *Chemical Abstracts* 117 (17) 789 column 1 abst. No. 170916e (Oct. 26, 1992).

*Primary Examiner*—John Kight
*Assistant Examiner*—Raymond Covington
*Attorney, Agent, or Firm*—Gilbert T. Voy

[57] ABSTRACT

The instant invention provides intermediates and processes for the preparation of compounds of formula IV

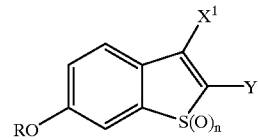

IV wherein:
n is 0, 1, or 2;
R is hydrogen or $C_1$–$C_4$ alkyl;
$X^1$ is hydrogen, cyano, 4-hydroxybenzoyl, 4-halobenzoyl, or 4-($C_1$–$C_4$ alkoxy)benzoyl;
Y is $NR^4R^5$, 4-hydroxyphenyl, or 4-($C_1$–$C_4$ alkoxy) phenyl;
and $R^4$ and $R^5$ are independently hydrogen or $C_1$–$C_4$ alkyl.

9 Claims, No Drawings

INTERMEDIATES AND A PROCESS FOR PREPARING BENZO[B]THIOPHENES

The application is a continuation of Provisional application No. 60/045,171 filed Apr. 30,1997 now abandoned.

TECHNICAL FIELD

The present invention relates to intermediates and processes for preparing benzo[b]thiophene compounds.

BACKGROUND OF THE INVENTION

The compound 6-hydroxy-2-(4-hydroxyphenyl)-3-[4-(2-piperidinoethoxy)benzoyl]benzo[b]thiophene, known also by its generic chemical name, raloxifene, is an important member of the class of compounds known as selective estrogen receptor modulators (SERMs). That compound is disclosed and claimed in U.S. Pat. No. 4,418,068.

One synthetic route for the preparation of benzo[b] thiophenes is disclosed in U.S. Pat. Nos. 5,606,075 and 5,606,076, and involves a compound of formula

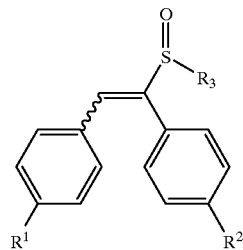

I wherein $R^1$ and $R^2$ are independently hydrogen, $C_1$–$C_4$ alkoxy, aryloxy, halo, or amino, and $R^3$ is a thermally labile or acid labile group. This intermediate is cyclized in the presence of an acid catalyst to form a compound of formula II

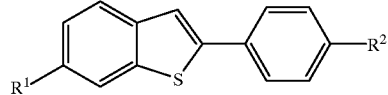

II

While this and other methods provide synthetic routes to benzo[b]thiophenes, a more efficient synthesis of benzothio[b]thiophenes is desirable. An improved synthetic route would preferably consist of fewer steps, be applicable to the preparation of 3-bromo-benzo[b]thiophenes, for example, and have milder reaction conditions. In addition, in the event that the starting materials or other reagents necessary for the processes described in the aforementioned United States patents are unavailable, it would be advantageous to have alternative commercial processes for the preparation of benzo[b]thiophenes. The present invention provides novel intermediates and novel synthetic routes for preparing intermediates, as well as for preparing substituted benzo[b] thiophenes.

SUMMARY OF THE INVENTION

The present invention provides a process for preparing compounds of formula IV

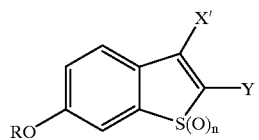

IV wherein:
n is 0 or 1;
R is a hydroxy protecting group;
X' is hydrogen, 4-hydroxybenzoyl, 4-halobenzoyl, 4-nitrobenzoyl, 4-($C_1$–$C_4$ alkoxy)benzoyl or Lg;
Lg is a leaving group selected from p-tolunesulfonyl-O—, phenylsulfonyl-O—, trifluoromethylsulfonyl-O—, isobutyl-O—, or $CH_3CO$—O—;
Y is $NR^4R^5$ or

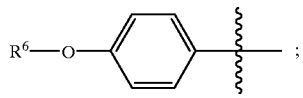

;

$R^4$ and $R^5$ are independently $C_1$–$C_4$ alkyl, or combine to form, together with the nitrogen to which they are attached, a piperidinyl, pyrrolidinyl, methylpyrrolidinyl, dimethylpyrrolidinyl, morpholino, dimethylamino, diethylamino, or 1-hexamethyleneimino ring; and
$R^6$ is a hydroxy protecting group; which includes reacting a compound of formula III

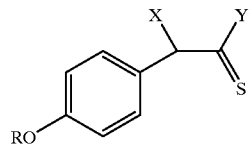

III wherein:
X is hydrogen, hydroxy, halo, 4-hydroxybenzoyl, 4-halobenzoyl, 4-nitrobenzoyl, 4-($C_1$–$C_4$ alkoxy) benzoyl or Lg; and
R and Y are as defined above; with a suitable acid and, when X is not halo, hydroxy, or Lg, in the presence of an oxidant.

The present invention further relates to processes for preparing compounds of formula V

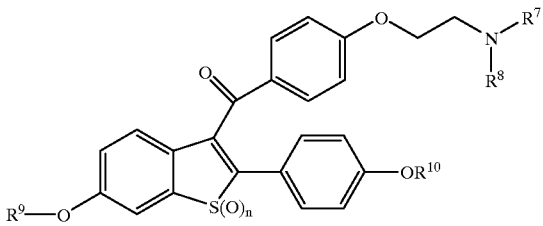

V wherein:
n is 0 or 1;

R[7] and R[8] are independently $C_1$–$C_4$ alkyl, or combine to form, together with the nitrogen atom to which they are attached, a piperidinyl, pyrrolidinyl, methylpyrrolidinyl, dimethylpyrrolidinyl, morpholino, dimethylamino, diethylamino, or 1-hexamethyleneimino ring; and R[9] and R[10] are independently hydrogen or hydroxy protecting groups; or a pharmaceutically acceptable salt or solvate thereof, from compounds of formula IV.

Also provided by the instant invention are compounds of formula III useful as intermediates in the chemical processes described above:

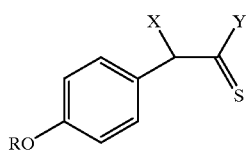

III wherein R, X, and Y are as defined above.

DETAILED DESCRIPTION OF THE INVENTION

The terms employed herein have the meanings typically ascribed to them in the art. The term "$C_1$–$C_6$ alkyl" denotes a monovalent radical derived from methane, ethane, or a straight or branched-chain saturated hydrocarbon of 3–6 carbon atoms by the removal of a single hydrogen atom and includes n-propyl, isopropyl, n-butyl, sec-butyl, isobutyl, tert-butyl, n-pentyl, isopentyl, 2-methylbutyl, hexyl, and the like. The term "lower alcohols" refers to $C_1$–$C_4$ alcohols including methanol, ethanol, propanol, isopropanol, butanol, n-butanol, isobutanol, t-butanol, and the like. The term "$C_1$–$C_4$ alkoxy" refers to a straight or branched alkyl chain having from one to four carbon atoms attached to the parent molecular moiety through an oxygen atom. Typical $C_1$–$C_4$ alkoxy groups include methoxy, ethoxy, propoxy, isopropoxy, n-butoxy, t-butoxy, and isobutoxy. The term "optionally substituted phenyl" refers to an unsubstituted phenyl group or a phenyl group substituted with one or two groups independently selected from $C_1$–$C_6$ alkyl, $C_1$–$C_4$ alkoxy, hydroxy, nitro, chloro, fluoro, or tri(chloro or fluoro) methyl. The term "halo" refers to fluoro, chloro, bromo, and iodo.

The term "Lewis acid catalyst" refers to the type of catalyst described in Olah, "Friedel-Crafts and Related Reactions," Interscience Publishing Co., New York, 1963 and includes metal halides such as aluminum bromide, aluminum chloride, boron trifluoride, boron trichloride, boron tribromide, titanium tetrachloride, titanium tetrabromide, stannic chloride, stannic bromide, bismuth trichloride, ferric chloride and the like.

The term "hydroxy protecting group" denotes a group understood by one skilled in the organic chemical arts of the type described in Chapter 2 of "Protective Groups in Organic Synthesis, 2nd Edition, T. H. Greene, et al., John Wiley & Sons, New York, 1991, hereafter "Greene".

Representative hydroxy protecting groups include, for example, —$C_1$–$C_4$ alkyl, —CO—($C_1$–$C_6$ alkyl), —$SO_2$—($C_4$–$C_6$ alkyl), and —CO—Ar in which Ar is optionally substituted phenyl. More specifically, other hydroxy protecting groups include, for example, ether groups, including methyl and substituted methyl ether groups such as methyl ether, methoxymethyl ether, methylthiomethyl ether, tert-buylthiomethyl ether, (phenyldimethylsilyl)methoxymethyl ether, benzyloxymethyl ether, p-methoxy-benzyloxymethyl ether, and tert-butoxy-methyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorobenzyl ether; and alkylsilyl ether groups such as trimethyl- triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono- di- and trichloroacetate esters, phenoxyacetate ester, and p-chlorophenoxyacetate and the like. The species of hydroxy protecting group employed is not critical so long as the derivatized hydroxy group is stable to the condition of subsequent reaction(s) on other positions of the intermediate molecule and can be selectively removed at the appropriate point without disrupting the remainder of the molecule including any other hydroxy protecting group(s). The selection of appropriate hydroxy protecting groups is within the knowledge of one skilled in the art for a given set of reaction conditions, given the guidance provided by Greene above. A preferred embodiment of this invention is where Y is 4-methoxyphenyl in compounds of formula IV. Another particularly preferred embodiment of this invention is where R[9] and R[10] are both methyl in compounds of formula V.

As mentioned above, the invention includes the pharmaceutically acceptable salts of the compounds defined by formula V. Although generally neutral, a compound of this invention can possess a sufficiently basic functional group, and accordingly react with any of a number of inorganic and organic acids, to form a pharmaceutically acceptable salt. See, for example, Berge, S. M, Bighley, L. D., and Monkhouse, D. C., *J. Pharrm. Sci.*, 66, 1, 1977.

The term "pharmaceutically acceptable salt" as used herein refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

It should be recognized that the particular counterion forming a part of any salt of this invention is not of a critical nature, so long as the salt as a whole is pharmacologically acceptable and as long as the counterion does not contribute undesired qualities to the salt as a whole.

The term "suitable aprotic solvent" refers to a solvent which does not contain any acidic protons, is inert to the ongoing reaction, and sufficiently solubilizes the reactants to effect the desired reaction. Examples of aprotic solvents include methylene chloride, chloroform, 1,2-dichloroethane, diethyl ether, acetonitrile, ethyl acetate, 1,3-dimethyl-2-imidazolidinone, tetrahydrofuran, dimethylformamide, toluene, chlorobenzene, dimethylsulfoxide, mixtures thereof, and the like.

The term "suitable protic solvent" refers to a solvent which contains an acidic proton, is inert to the ongoing reaction, and sufficiently solubilizes the reactants to effect the desired reaction. Examples of protic solvents include lower alcohols, water, mixtures thereof, and the like.

The term "suitable kinetic base" refers to a strong base which provides a non-reversible deprotonation of an acidic substrate and is reactive enough to effect the desired reaction without significantly effecting any undesired reactions. Examples of kinetic bases include alkyl metals (for example, n-butyl lithium, s-butyl lithium, and t-butyl lithium or ethyl magnesium bromide and the like), metal amides such as lithium diisopropyl amide, metal alkoxides such as potassium t-butoxide, or metal hydrides (for example, sodium, lithium, or potassium hydride).

The term "suitable thermodynamic base" refers to a base which provides a reversible deprotonation of an acidic substrate and is reactive enough to effect the desired reaction without significantly effecting any undesired reactions. Examples of thermodynamic bases include carbonates, bicarbonates, and hydroxides (for example, lithium, sodium, or potassium carbonate, bicarbonate, or hydroxide).

The term "suitable acid" refers to any acid reactive enough to effect the desired reaction without significantly effecting any undesired reactions. The skilled artisan will recognize that the reactivity of an acid relates to the ability to donate a proton (Bronsted acidity) or to the ability to accept an electron pair (Lewis acidity). Examples of suitable acids include inorganic acids, such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

The term "suitable base" refers to any base reactive enough to effect the desired reaction without significantly effecting any undesired reactions. The skilled artisan will recognize that the reactivity of a base relates to the ability to donate a hydroxide ion (Bronsted basicity) or to the ability to donate an electron pair (Lewis basicity).

While all of the compounds of this invention are useful in the production of substituted benzo[b]thiophenes, certain classes of compounds are preferred. The following describes the preferred classes of compounds of formulae III, IV and V:

aa) R is methyl;
ab) R is hydrogen;
ac) R is isopropyl;
ad) X is hydrogen;
ae) X is 4-methoxybenzoyl;
af) X is 4-hydroxybenzoyl;
ag) X is 4-halobenzoyl
ah) X is 4-fluorobenzoyl;
ai) X is 4-chlorobenzoyl;
aj) X is 4-bromobenzoyl;
ak) X is 4-iodobenzoyl;
al) Y is —NR$^4$R$^5$;
am) Y is 4-hydroxyphenyl;
an) Y is 4-methoxyphenyl;
ao) Y is dimethylamino;
ap) Z is halo;
aq) Z is fluoro;
ar) Z is chloro;
as) Z is bromo;
at) Z is iodo; and
au) R$^4$ and R$^5$ are methyl
av) X$^1$ is halo;
aw) X$^1$ is bromo;
ax) X$^1$ is chloro;
az) X$^1$ is iodo;
ba) X$^1$ is hydroxy.

It will be understood that the above classes may be combined to form additional preferred classes.

The following group is illustrative of compounds contemplated within the scope of this invention:
4-methoxy-4'-isopropoxy thiodeoxybenzoin;
4-hydroxy-4'-methoxy thiodeoxybenzoin;
4-methoxy-4'-hydroxyoxy thiodeoxybenzoin;
α-(4-methoxybenzoyl)-4-methoxy-4'-isopropoxy thiodeoxybenzoin;
α-(4-fluorobenzoyl)-4-methoxy-4'-isopropoxy thiodeoxybenzoin;
α-(4-nitrobenzoyl)-4-methoxy-4'-isopropoxy thiodeoxybenzoin
N,N-dimethyl(4-methoxyphenyl)thioacetamide
N-methyl-N-ethyl (4-methoxyphenyl)thioacetamide
N-isopropyl-N-butyl (4-hydroxyphenyl)thioacetamide
N,N-dimethyl(4-benzyloxyphenyl)thioacetamide; and
α-(4-methoxybenzoyl)-N,N-dimethyl-(4-methoxyphenyl) thioacetamide.

A portion of the overall process of the instant invention is depicted in Scheme I below, wherein halo, R, X, X', Y, and Z are as defined, infra.

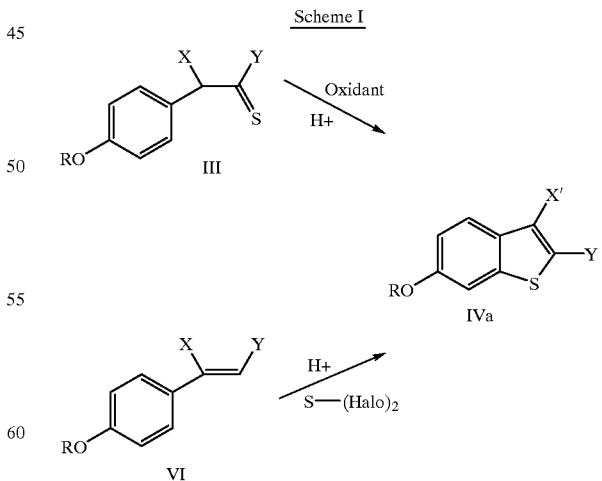

If X is hydroxy or halo in the starting compounds of formula III and VI, the hydroxy or halo group will be removed during the reactions shown in Scheme I to generate compounds of formula IV wherein X' is hydrogen. Compounds of formula IV include compounds of formula IVa (wherein n is 0) and IVb (wherein n is 1). Compounds of formula IV where n is 0 may be prepared by the halogenation of compounds of formula III or compounds of formula VI. For example, the transformation from a compound of formula III to a compound of formula IVa is typically carried out by dissolving or suspending a suitable acid in an suitable aprotic or protic solvent, then adding a compound of formula III and an oxidant. Suitable oxidants include halogenating reagents. Suitable halogenating reagents include benzeneseleninylchloride/aluminum chloride, thionyl chloride, CsSO$_4$F, NFTh, N-bromo succinimide, N-chloro succinimide, N-iodo succinimide, and the like. Molecular bromine or iodine are the preferred oxidants. An aprotic solvent is generally preferred, and chlorobenzene is particularly preferred. p-Toluene sulfonic acid is the preferred acid. The acid is generally and preferably employed in a stoichiometric amount. The oxidant is generally employed in a slight deficiency. For example, a 95 to 100 molar percent, relative to the compounds of formula III, is generally employed. A 97 molar percent is typically preferred. The reaction is preferably carried out at about the reflux temperature of the solvent for about 15 minutes.

The transformation from a compound of formula VI to a compound of formula IVa is performed in a similar manner to that described for III to IVa, except that a halogenating reagent of the formula S-(halo)$_2$ is employed. Preferred compounds of the formula S-(halo)$_2$ are sulfur dichloride, dibromide, and diiodide.

The compounds of formula IV where n is 1 may be prepared from compounds of formula VII by subjecting appropriately substituted ketones of formula VII to a halogenating reagent of the formula SO-(halo)$_2$. This chemistry is depicted in Scheme II below where halo, R, X, X$^1$, and Y are as defined, supra.

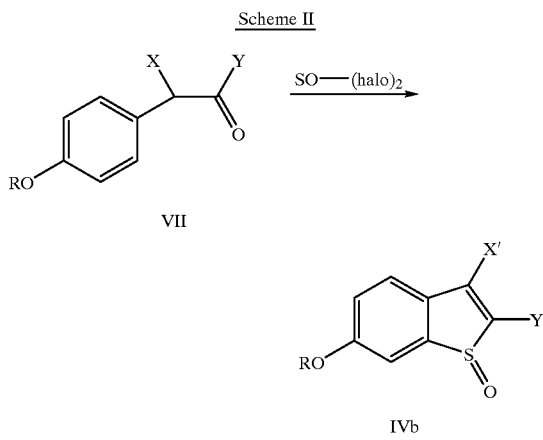

Scheme II

Compounds of formula IVb may be prepared by sulfenation/halogenation of compounds of formula VII. For example, a compound of the formula SO-(halo)$_2$ may be added to a compound of formula VII, dissolved or suspended in a suitable aprotic or protic solvent. Suitable halogenating reagents include thionyl chloride, thionyl bromide, and the like. The halogenating reagent is generally and preferably employed in a stoichiometric amount, relative to the compounds of formula VII.

Compounds of formula IV may be converted to compounds of formula V. For example, when X' is hydrogen, a compound of formula V may be acylated with a compound of formula VIII

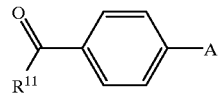

VIII wherein R$^{11}$ is hydroxy, chloro, bromo, or iodo; A is halo, nitro, hydroxy, C$_1$–C$_4$ alkoxy, —O—(CH$_2$)$_2$—Z', or —O—(CH$_2$)$_2$—NR$^7$R$^8$; Z' is halo or p-toluenesulfonyl; and R$^7$ and R$^8$ are as defined, supra, in the presence of boron trichloride or boron tribromide, as taught in U.S. Pat. No. 5,606,075, the disclosure of which is herein incorporated by reference. When Y is —NR$^4$R$^5$ in a compound of formula IV, the acylation is preferably run not in the presence of boron trichloride or tribromide, but instead in the presence of a protic acid as is taught in U.S. Pat. No. 5,420,349, the disclosure of which is herein incorporated by reference. When A is not —O—(CH$_2$)$_2$—NR$^7$R$^8$, the product of the acylation reaction may be converted to a compound of formula V by the methods described herein.

Compounds of formula IV, where X' is 4-halobenzoyl or 4-nitrobenzoyl, may be converted to compounds of formula V. For example, a compound of the formula HO—(CH$_2$)$_2$—NR$^7$R$^8$, dissolved or suspended in a polar aprotic solvent, in the presence of a suitable kinetic or thermodynamic base, may be reacted with a compound of formula IV where X' is 4-halobenzoyl or 4-nitrobenzoyl. Dimethylformamide is the preferred solvent. A kinetic base, specifically sodium hydride, is typically the preferred base.

Compounds of formula IV where X' is 4-hydroxybenzoyl may be converted to compounds of formula V by dissolving a compound of formula IV in a suitable protic or aprotic solvent, in the presence of a suitable base, and adding a compound of the formula Z'—(CH$_2$)$_2$—NR$^7$R$^8$, where Z', R$^7$, and R$^8$ are as defined herein. Dimethylsulfoxide is the preferred solvent. A kinetic base, sespecially sodium hydride, is the preferred base. The base is typically employed in a slight molar excess. For example, a 1.01 to 1.15 molar excess, relative to the compound of formula IV is generally employed. A 1.05 molar excess is preferred. The compound of formula Z'—(CH$_2$)$_2$—NR$^7$R$^8$ is typically employed in a slight molar excess. For example, a 1.01 to 1.15 molar excess, relative to the starting compound of formula IV, is generally employed. A 1.05 molar excess is typically preferred. The reaction is preferably carried out at about 35° C. for about 2 hours after addition of the base, and then at about 65° C. for about 16 hours after the addition of a compound of formula Z'—(CH$_2$)$_2$—NR$^7$R$^8$.

Compounds of formula IV where X' is 4—(C$_1$–C$_4$ alkoxy) benzoyl may be converted to compounds of formula V where A is hydroxy by first removing the C$_1$–C$_4$ alkyl group as described in the DEPROTECTION section below to give the compound of formula V where X' is 4-hydroxybenzoyl and then converting the resulting compound by the method of the previous paragraph.

DEPROTECTION

In general, methods for protecting hydroxy groups with one of the groups listed above, or in Greene, and for cleaving or removing the protecting groups to afford compounds of formula V, where R$^9$ and R$^{10}$ are hydrogen, may be found in Greene and are well known to one skilled in the art.

More specifically, compounds of formula V where R$^9$ or R$^{10}$ are —CO—(C$_1$–C$_6$ alkyl) or —CO—Ar may be deprotected by the methods taught in U.S. Pat. No. 4,358,593, the disclosure of which is herein incorporated by reference.

In addition, compounds of formula V where R$^9$ or R$^{10}$ are methyl may be deprotected by the use of thiol reagents as taught in U.S. Pat. No. 4,380,635, the disclosure of which is herein incorporated by reference.

A compound of formula V where $R^9$ or $R^{10}$ are $C_1$–$C_4$ alkyl, may be dissolved in a suitable solvent, and a Lewis acid added. Methylene chloride is typically the preferred solvent. Boron trichloride is typically the preferred Lewis acid. The Lewis acid is generally employed in a substantial molar excess. For example, a 2 to 4 molar excess, relative to the compound of formula V, is generally employed. A 3 molar excess is typically preferred. The reaction is typically and preferably carried out at about 35° C. for about 4 to 48 hours.

The skilled artisan will further appreciate that if a particular hydroxy protecting group is desired in a compound of formula V, but that hydroxy protecting group is incompatible to a particular choice of reaction pathways of the invention, the desired hydroxy protecting group can be reattached as a last step in the synthesis according to well known methods in the art, for example, those methods described in Greene.

When Y is —$NR^4R^5$, in compounds of formula IV, the synthesis of compounds of formula V should include the reaction of said compound of formula IV with a compound of formula IX

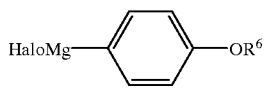

IX as taught in U.S. Pat. No. 5,420,349. The Grignard addition is generally and preferably performed after the acylation with a compound of formula VIII. However, when X' is 4-nitrobenzoyl in compounds of formula IV, or when A is nitro in compounds of formula VIII, the displacement of the nitro group must occur before the Grignard addition due to incompatibilities of the nitro group with Grignard reagents.

Furthermore, the skilled artisan will recognize that compounds of formula IV or V where n is 1 may be converted to compounds of formula IV or V where n is 0 or vice versa by methods well known in the art. For example, benzothiophene oxides (where n is 1) may be obtained by treating benzothiophenes with m-chloroperbenzoic acid. Benzothiophene oxides may be converted into benzothiophenes (n is 0) by an appropriate reducing agent such as sodium iodide/$SO_3$/pyridine.

The starting materials of the processes of the invention may be made from compounds of formula III. For example, a compound of formula VII may be treated with a sulfenating reagent. This chemistry is illustrated in Scheme III below, where R, X, and Y are as defined, supra.

Scheme III

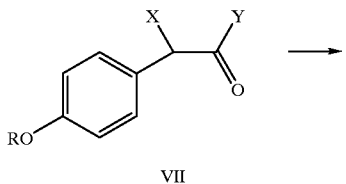

VII

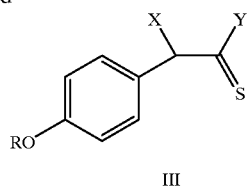

III

Compounds of formula III may be prepared from compounds of formula VII. For example, a compound of the formula VII, dissolved or suspended in a suitable aprotic or protic solvent, may be treated with a sulfenating reagent. Suitable sulfenating reagents include phosphorous pentasulfide (See, for example, *Syn. Comm.*, 3085, 1990), hydrogen sulfide in the presence of a suitable acid, or Lawesson's Reagent. In addition, compounds of formula VII, where X is halo, hydroxy, or Lg, may be converted directly to compounds of formula IV where $X^1$ is hydrogen by similar reaction with a sulfenating reagent in the presence of a suitable acid. This conversion is illustrated in Scheme IV below, where X is hydroxy, halo, or Lg.

Scheme IV

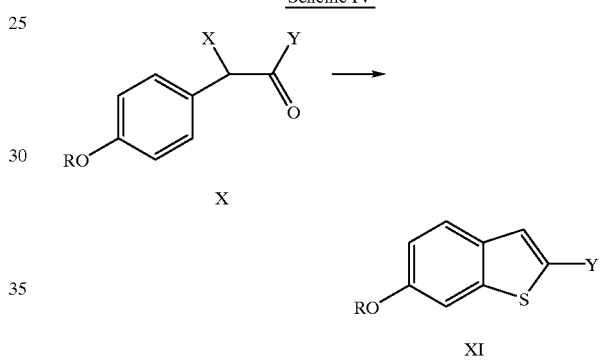

A preferred sulfenating reagent for this transformation is phosphorous pentasulfide.

Compounds of formula III where Y is $NR^4R^5$, may also be prepared from the corresponding acetophenones by the Willgerodt reaction.

For additional methods of preparing compounds of formula III, the skilled artisan may consult Ohno, "Organic Chemistry of Sulfur", pp 189–229, Plenum, N.Y., 1977 or Mayen, "Organosulfur Chemistry", pp 219–240, Wiley Interscience, N.Y., 1967.

In general, the reactions of Schemes I–IV are substantially complete in about 15 minutes to 72 hours when conducted at a temperature range of from about 0° C. to the reflux temperature of the reaction mixture. The reaction solvent choice is not critical so long as the solvent employed is inert to the ongoing reaction and the reactants are sufficiently solubilized to effect the desired reaction. The compounds of formula III–XI are preferably isolated and purified before use in subsequent reactions.

The following Preparations and Examples further illustrate specific aspects of the present invention. It is to be understood, however, that these examples are included for illustrative purposes only and are not intended to limit the scope of the invention in any respect and should not be so construed.

EXAMPLES

In the following Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. The values reported for MS(FD) correspond to mass numbers unless otherwise indicated. In addition, the absorption maxima listed for the IR spectra are only those of interest and not all of the maxima observed.

Example 1

Thiodesoxyanisoin

Step 1: Formation of the Dimethyl Ketal of Desoxyanisoin 100 ml of methanol, para toluene sulfonic acid mono hydrate (580 mg, 3.00 mmol), and desoxyanisoin (20.0 g, 78 mmol) are placed in a 3 neck round bottom flask fitted with a condenser, magnetic stirrer, nitrogen inlet, thermometer, and heating mantle. Trimethyl orthoformate is added (100 ml) and the solution heated to reflux for 3.5 hours. Potassium carbonate (13.82 g, 100 mmol) is added and the reaction allowed to cool to room temperature. The solid that forms is filtered off and washed with 50 ml of methanol. The filtrate is concentrated down to give 17.4 g of the product as a semi-solid. (73.7%). NMR.

Step 2: Formation of Thiodesoxyanisoin

The product of step 1 (6.04 g, 20 mmol), zinc chloride (140 mg, 1.00 mmol), and 2 ml of ethanol are placed in a 25 ml, 3-neck round bottom flask fitted with a thermometer, gas inlet, gas outlet to a bleach/caustic scrubber, and a magnetic stirrer. The mixture is cooled to 0° C. and hydrogen sulfide is bubbled through the solution for 30 minutes. Pentane (150 ml) and toluene (50 ml) are added and the mixture is washed with 50 ml of 0.1 N aqueous hydrochloric acid, 50 ml of water, and 50 ml of 20% aqueous sodium chloride. The organic layer is separated and concentrated to give 4.9 g of a 60:40 mixture of product to ketone starting material. (53.9% adjusted yield). MS(FD), NMR.

Example 2

2-(4-Methoxyphenyl)-6-Methoxybenzothiophene

The p-toluene sulfonic acid mono hydrate (310 mg, 1.6 mmol) in 25 ml of chlorobenzene is placed in a 25 ml, 3-neck round bottom flask fitted with a thermometer, nitrogen gas inlet, 10 ml addition funnel, reflux condenser, Dean-Stark trap with drying tube, magnetic stirrer, and heating mantle. 10 ml of solvent is distilled off and bromine (0.08 ml, 1.55 mmol) is added followed by thiodesoxyanisoin (700 mg, 1.6 mmol) in 10 ml of chlorobenzene over 5 minutes. After stirring at reflux for 15 minutes the reaction is allowed to cool to room temperature. A precipitate forms and is filtered off. The filter cake is washed with 50 ml of chlorobenzene. The filtrate is washed with water (2×50 ml), 5% sodium bicarbonate, 50 ml water, and 50 ml of 10% aqueous sodium chloride. The organics are dried over sodium sulfate and concentrated. The crude product is purified by silica gel chromatography then triturated with chlorobenzene. The side product solid is filtered off and the filtrate concentrated. The residue is triturated with ethyl acetate and filtered to give 10.8 mg of pure product. (0.25%). $^1$H NMR.

Example 3

Alternate Synthesis of 2-(4-Methoxyphenyl)-6-Methoxybenzothiophene

Anisoin (2.87 g), 50 ml of chlorobenzene, and Lawesson's Reagent 4.04 g are placed in a flask under nitrogen. The mixture is heated to 100° C. and a methanesulfonic acid (0.65 mL) is added and the mixture heated at reflux for 92 hours. The reaction is cooled to room temperature before filtering the solids which form. The filter cake is washed with 25 ml of chlorobenzene and dried to give 270 mg of product. The solid is recrystallized from hot chlorobenzene to give 90 mgs of pure product. Analysis calculated for $C_{16}H_{14}O_4S$: C, 71.08; H, 5.22; S, 11.86. Found: C, 71.27; H, 5.43; S, 11.78. MS.

Example 4

Alternate Synthesis of 2-(4-Methoxyphenyl)-6-Methoxybenzothiophene

Step 1: Preparation of α-Chloro-Deoxyanisoin

Anisoin (2.87 g), 100 mL of methylene chloride, and pyridine (2.02 g) are placed in a flask under nitrogen. Thionyl chloride (1.60 ml) is added dropwise over 5 minutes using a water bath to maintain the reaction temperature between 25° C. and 30° C. After allowing the mixture stir for 50 minutes the reaction is quenched by washing with water (2×100 mL) and 100 mL of brine. The organics are dried over sodium sulfate, filtered, then concentrated. The resulting oil is taken up in 25 mL of diethyl ether and filtered. The filter cake is rinsed with 25 ml of diethyl ether. To the filtrate is added 25 ml of ethanol and the solution is concentrated. Crystals are allowed to form over 24 hours. The precipitate which forms is filtered, washed with 25 mL of ethanol, and dried in vacuo at 45° C. to give 4.00 g of product. (69%). Analysis calculated for $C_{16}H_{14}ClO_3$: C, 66.10; H, 5.20; Cl, 12.19. Found: C, 66.29; H, 5.32; Cl, 12.56. MS(FD) 290.

Step 2: Preparation of 2-(4-Methoxyphenyl)-6-Methoxybenzothiophene

α-Chloro-deoxyanisoin (580 mg) is converted to product by the procedure of Example 3 to give 128 mg. (24%). $^1$H NMR, HPLC.

Example 5

Alternate Synthesis of 2-(4-Methoxyphenyl)-6-Methoxybenzothiophene

Anisoin is converted to product by the procedure of Example 4, Steps 1 and 2 to yield 210 mg. (18%). $^1$H NMR, HPLC.

We claim:

1. A process for preparing a compound of formula IV

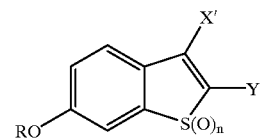

IV wherein:

n is 0 or 1;

R is hydrogen or $C_1$–$C_4$ alkyl;

X' is hydrogen, 4-hydroxybenzoyl, 4-halobenzoyl, 4-nitrobenzoyl, or 4-($C_1$–$C_4$ alkoxy)benzoyl;

Y is $NR^4R^5$ or

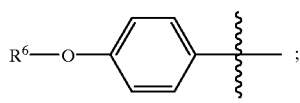

$R^4$ and $R^5$ are independently $C_1$–$C_4$ alkyl; and
$R^6$ is a hydroxy protecting group;
which comprises:
reacting a compound of formula VII

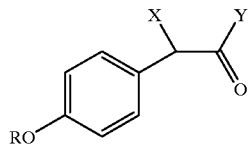

wherein
X is hydrogen, halo, hydroxy, 4-hydroxybenzoyl, 4-halobenzoyl, 4-nitrobenzoyl, 4-($C_1$–$C_4$ alkoxy) benzoyl, or Lg;
Lg is p-tolunesulfonyl-O—, phenylsulfonyl-O—, trifluoromethylsulfonyl-O—, isobutyl-O—, or $CH_3CO$—O—;
and R and Y are as defined above;
with a sulfenating reagent,
with the proviso that when X' is not halo, hydroxy, or Lg, the product is additionally reacted with an oxidant in the presence of a suitable acid;
and optionally reducing the benzothiophene sulfur.

2. A process according to claim 1 wherein X is hydrogen.

3. A process according to claim 1 wherein X is halo, hydroxy, or Lg.

4. A process for preparing a compound of formula IV

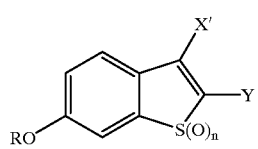

wherein:
n is 0 or 1;
R is hydrogen or $C_1$–$C_4$ alkyl;
X' is hydrogen, 4-hydroxybenzoyl, 4-halobenzoyl, 4-nitrobenzoyl, or 4-($C_1$–$C_4$ alkoxy)benzoyl;
Y is $NR^4R^5$ or

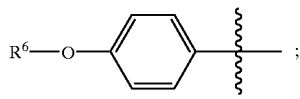

$R^4$ and $R^5$ are independently hydrogen or $C_1$–$C_4$ alkyl; and
$R^6$ is a hydroxy protecting group;
which comprises:

reacting a compound of formula III

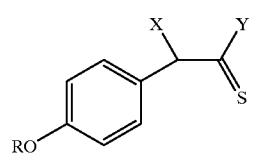

wherein

R is a hydroxy protecting group;
X is hydrogen, halo, hydroxy, 4-hydroxybenzoyl, 4-halobenzoyl, 4-nitrobenzoyl, 4-($C_1$–$C_4$ alkoxy) benzoyl, or Lg;
Lg is p-tolunesulfonyl-O—, phenylsulfonyl-O—, trifluoromethylsulfonyl-O—, isobutyl-O—, or $CH_3CO$—O—;
Y is $NR^4R^5$ or

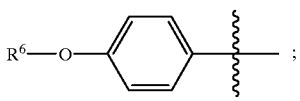

$R^4$ and $R^5$ are independently $C_1$–$C_4$ alkyl; and
$R^6$ is a hydroxy protecting group;
with an oxidant and a suitable acid,
and optionally reducing the benzothiophene sulfur.

5. A process according to claim 1 which further comprises acylating a compound of formula IV wherein X' is hydrogen with a compound of formula VIII

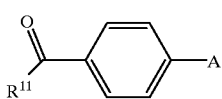

wherein:

$R^1$ is hydroxy, chloro, bromo, or iodo;
A is halo, nitro, hydroxy, $C_1$–$C_4$ alkoxy, —O—$(CH_2)_2$—Z', or —O—$(CH_2)_2$—$NR^7R^8$;
$R^7$ and $R^8$ are independently $C_1$–$C_4$ alkyl, or combine to form, together with the nitrogen to which they are attached, a piperidinyl, pyrrolidinyl, methylpyrrolidinyl, dimethylpyrrolidinyl, morpholino, dimethylamino, diethylamino, or 1-hexamethyleneimino ring; and
Z' is halo or p-toluenesulfonyl;

and optionally removing the hydroxy protecting groups, to provide a compound of formula XII

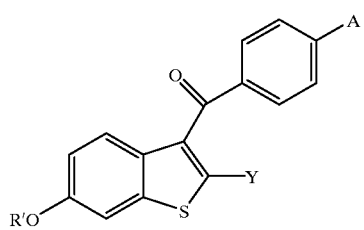

wherein R' is hydrogen or a hydroxy protecting group and Y and A are as defined above.

6. A compound of formula III

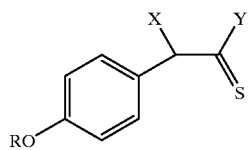

wherein

R is a hydroxy protecting group;

X is hydrogen, halo, hydroxy, 4-hydroxybenzoyl, 4-halobenzoyl, 4-nitrobenzoyl, 4-($C_1$–$C_4$ alkoxy)benzoyl, or Lg;

Lg is p-tolunesulfonyl-O—, phenylsulfonyl-O—, trifluoromethylsulfonyl-O—, isobutyl-O—, or $CH_3CO$—O—;

Y is

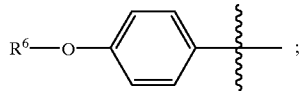

$R^4$ and $R^5$ are independently $C_1$–$C_4$ alkyl; and $R^6$ is a hydroxy protecting group.

7. A compound according to claim 6 wherein X is hydrogen.

8. A compound according to claim 6 wherein Y is

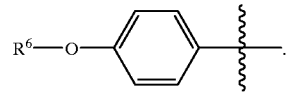

9. A compound according to claim 8 wherein R and $R^6$ are both methyl.

* * * * *

UNITED STATES PATENT AND TRADEMARK OFFICE
CERTIFICATE OF CORRECTION

PATENT NO.    : 6,043,360
DATED         : March 28, 2000
INVENTOR(S)   : Tony Yantao Zhang and John Paul Gardner It is certified that error appears in the above-identified patent and that said Letters Patent is hereby corrected as shown below:

Column 14,
Line 53, should read "$R^{11}$ is hydroxy, chloro, bromo, or iodo;"

Signed and Sealed this

Fifth Day of February, 2002

Attest:

JAMES E. ROGAN
Attesting Officer    Director of the United States Patent and Trademark Office